United States Patent [19]

Super

[11] Patent Number: 5,235,361
[45] Date of Patent: Aug. 10, 1993

[54] STEREOSCOPIC VISION TESTING APPARATUS

[76] Inventor: Selwyn Super, 309 The Albany, 8 Atherstone Road, Illovo; Johannesburg, Transvaal, South Africa

[21] Appl. No.: 805,314

[22] Filed: Dec. 10, 1991

[30] Foreign Application Priority Data

Dec. 12, 1990 [ZA] South Africa ............... 90/9986

[51] Int. Cl.⁵ ............................ A61B 3/02; A61B 3/08
[52] U.S. Cl. .............................. 351/240; 351/201; 351/202; 351/246
[58] Field of Search ............... 351/201, 202, 240, 247, 351/246, 244, 245

[56] References Cited

U.S. PATENT DOCUMENTS 2,362,588  11/1944  Shepard ..................... 351/201

Primary Examiner—Rodney B. Bovernick
Attorney, Agent, or Firm—Sheldon & Mak

[57] ABSTRACT

Apparatus for use in optometry to determine the degree of stereo acuity present in a patient comprises a frame having a proximal end adapted to engage against the face, particularly the chin of the patient, and carrying a support structure for receiving a plurality of standardized stereograms to be capable of selectively being brought into the patient's line of vision. A test procedure utilizing the apparatus is also disclosed.

10 Claims, 3 Drawing Sheets

STEREOSCOPIC VISION TESTING APPARATUS

FIELD OF THE INVENTION

This invention relates to apparatus for use in optometry and the testing of binocular vision. More specifically this invention relates to an apparatus suitable for use in conducting tests of stereopsis.

BACKGROUND TO THE INVENTION

Stereopsis may be described as the ability to appreciate depth binocularly and to recognise the specific localization of form and its relative position to the observer and to other spatial objects. In layman's terms this amounts to three dimensional vision. This facility is not shared equally by all people. The inability to appreciate depth of vision binocularly may be caused by conditions such as strabismus or for other less apparent reasons. Approximately 95% of people enjoy some measure of stereopsis.

Stereopsis is regarded as one of the highest functions of the vision system and seems to have developed phylogenetically at the same time as the emancipation of man's hands. It is the coordinated visual control of man's hands which has been largely responsible for his intellectual and technological progress. It is well known that the visual acuity of sighted people varies and bears some relationship to their refractive states. In the same manner it has been found that people present with different degrees of stereo acuity, that is different degrees to which objects may be perceived to lie in different planes when viewed binocularly.

The retinal system is known to operate with many sub-systems which are receptive to movement, colour, edges, light intensities and contours which contribute to depth perception. Stereopsis does not rely on vision perception alone but calls for an integration of all of man's senses and motor systems to answer the questions of what, where and when objects are present in space. Stereopsis is accordingly regarded as the highest form of binocular vision and stereoscopic localization appears to be one of the first discriminations of which the human visual system is capable.

It is further known that there are many monocular cues which contribute to the appreciation of depth. However, since the late 1950's it has also been known that stereopsis is indeed possible in the absence of monocular form cues.

The increasing knowledge and understanding of the anatomy and physiology of the visual pathways provides researchers with a continually increasing understanding of the manner in which binocular vision is attained through the integration by binocular cells in the visual cortex of images that fall on corresponding regions of the retinae of both eyes. The role of the optic chiasma in this respect is now well understood. It is also known that the corpus callosum plays a role in stereopsis and that through these connections, disparate image information in each hemisphere of the brain is brought together to see stereoscopically. If the optic chiasma is cut longitudinally along its midline, this will give rise to bitemporal hemianopia and also a blind area beyond the point of regard. However, the patient will still be able to appreciate stereopsis in front of the plane of regard. If the corpus callosum is cut along its midline, as is done in some cases of Parkinson's disease or epilepsy, then this gives rise to local stereo-blindness within a narrow angle in front of, as well as behind, the plane of regard.

Vision care practitioners have for the past century used devices to determine whether their patients are able to see stereoscopically. One such device consists of the use of polarized stereo-vectograms which are used in conjunction with dissociating polarized viewers. Besides providing information about the quality of a patient's binocular vision, these tests may also be used to assist in the diagnosis of strabismus. Stereograms produced for this purpose are sold commercially by several manufacturers including Stereo Optical Company, Inc. of Chicago, Ill., United States of America. The most commonly used stereograms fall into two groups, namely those featuring contours which provide monocular cues as to the form or symbol in the stereograms, and those without such cues, which latter group is known as random dot stereograms. When viewing a stereogram of this nature through dissociating polarised lenses the patient with normal stereopsis perceives images of objects in the stereogram to be displaced either forwardly or rearwardly of the plane of regard or fixation being looked at. This illusion is achieved by creating on the stereogram a form having stereo disparity. The larger the degree of stereo disparity of the symbol being observed, the further it appears to be displaced relative to the plane of regard and hence the easier will it be for the patient to discriminate between the form and its reference ground. The ability to see the apparent displacement can hence be used as a measure of the patient's stereo acuity.

It is believed that valuable information about a patient's visual functions and ability to respond to visual stimuli can be obtained by means of an assessment of his or her stereo acuity both in static and dynamic mode. Such information can then be used to assess a person's spatial abilities which appear related to the level of his stereo-acuity and the speed with which he or she makes such judgments. The information may also be used to assess the value of any therapeutic regimen and its effects on the speed and acuity of stereopsis, e.g. medication, exercises or lenses. To date the available tests have not been standardized to allow for cross comparisons and to assess different stereoscopic performance conditions accurately.

OBJECT OF THE INVENTION

It is accordingly an object of the present invention to provide an apparatus suitable for use in carrying out standardized stereoscopic vision tests, particularly but not exclusively on children, even at the pre-school level. It is a further object of the invention to provide such an apparatus in a very simple form to minimize the risk of distractions to the patient during performance of the test.

GENERAL DESCRIPTION OF THE INVENTION

According to the present invention there is provided an apparatus suitable for use in conducting stereoscopic vision tests, the apparatus comprising an elongated frame structure defining a proximal end and a distal end, the proximal end being adapted to engage against the body of a test subject and the frame being adapted towards its distal end to carry a stereogram support structure in axially displaceable relationship relative to the proximal end to allow the stereogram to be placed at a selected distance from the proximal end of the apparatus.

According to one form of the invention the apparatus is a portable apparatus comprising a frame in the form of a rod. The rod preferably includes a transversely extending grip formation for use in holding the rod in operative disposition.

In a preferred form of the invention the proximal end of the rod is adapted in use to engage against the face of the test subject. Most preferably the apparatus is adapted to engage the chin of a test subject. Thus, in the preferred form of the invention the rod is fitted with a diverging fork formation at the proximal end thereof.

The stereogram support structure is preferably equipped with a base formation adapted to be mounted in sliding relationship on the rod. The base formation may include a clamp arrangement for use in clamping the base formation at a selected disposition relative to the proximal end of the rod. The clamp formation may thus comprise a winged screw-threaded stud located in a complementary threaded socket in the base formation to allow the leading end of the stud to be brought into urging contact with the rod thereby to hold the base formation against sliding at a preferred position along the rod.

The support structure may be of any suitable configuration. Thus, the support structure may comprise a generally rectangular U-shaped formation composed of three channel members collectively defining an open-topped frame structure into which a stereogram may be fitted.

In a preferred form of the invention, however, the support structure is in the form of a carousel-like arrangement adapted to carry a plurality of stereograms and allowing a selected stereogram to be brought into a selected line of vision when the apparatus is supported in operative disposition against the face of a test subject.

Thus, in one form of the invention the support structure may comprise a hub formation adapted to carry a disk member featuring a plurality of stereograms, the support structure being adapted in use to be rotated about the axis of the rod thereby to bring a selected sector of the disc featuring a selected stereogram into a line of vision extending along the rod.

In a preferred form of the invention, however, the support structure may be in the form of an irregular polyhedral structure defining a plurality of oblong rectangular faces, mounted for rotation about its longitudinal axis and disposed to extend normally upwardly from the rod when the apparatus is in operative disposition, the support structure thereby being adapted to be rotated about its longitudinal axis to bring a selected face into the normal line of vision of the test subject.

The support structure is preferably in the form of a hexahedron presenting four rectangular faces bridged at opposing ends by two bases, at least two of the faces defining an oblong rectangular receiving frame for a stereogram. Preferably three of the faces are adapted to carry stereograms.

The stereograms used in conjunction with the apparatus described above preferably comprise a group of three plates each of which features ten stereograms arranged in line with one another and each stereogram featuring one form having stereo disparity, the degree of stereo disparity of the stereo forms in successive stereograms being progressively smaller from one end of the plate to the other.

The stereo forms may be circles. In one of the stereogram plates the stereo forms are presented as contoured circles against a noise free background, in the second the circles which are invisible monocularly are represented against a noise background constituted by random dots and in the third plate the contoured circles are presented against a random dot noise background. In the first-mentioned two stereogram plates each stereogram zone preferably features two non-stereo forms along with the stereo form and the relative position of the stereo form and non-stereo forms are located in random arrangement. Again in the random dot stereogram plate the stereo circle form is randomly placed on either the left, right or centre in relation to its reference ground.

The invention further comprises a set of equipment for use in conducting tests of stereopsis comprising an apparatus and stereograms as described above and two stereo-viewers, one of which comprises a pair of dissociating polarized lenses in crossed form, i.e. the right eye sees the left stereogram target and the left eye sees the right stereogram target, and the other comprising a pair of dissociating polarized lenses in uncrossed form, i.e. the right eye sees the right stereogram target and the left eye sees the left stereogram target.

The equipment of the invention thus provides a means for conducting a standardised test to determine the subject's degree of stereo acuity at a specific viewing distance of vision.

In the most preferred form of the invention there is provided an integrated stereogram support structure carrying stereogram plates of the nature described above and wherein each form position of each stereogram has associated therewith a membrane switch which is operatively connected to a power source, a visible signal means and an audible signal generator, the support arrangement further including a timer arrangement, and an activator and deactivator for the timer arrangement.

The visible signal sources may be light sources connected to the switches and are preferably light emitting diodes [l.e.d.'s]. The audible signal generator is preferably a buzzer.

By means of this arrangement a test subject may start a test by activating the timer and then touching the figures recognised as having stereoscopic properties when looking at the stereogram through polarised lenses and deactivating the timer when the test is completed.

Without thereby limiting the scope of the invention some preferred embodiments will now be described with reference to the accompanying drawings in which.

Figure 1:
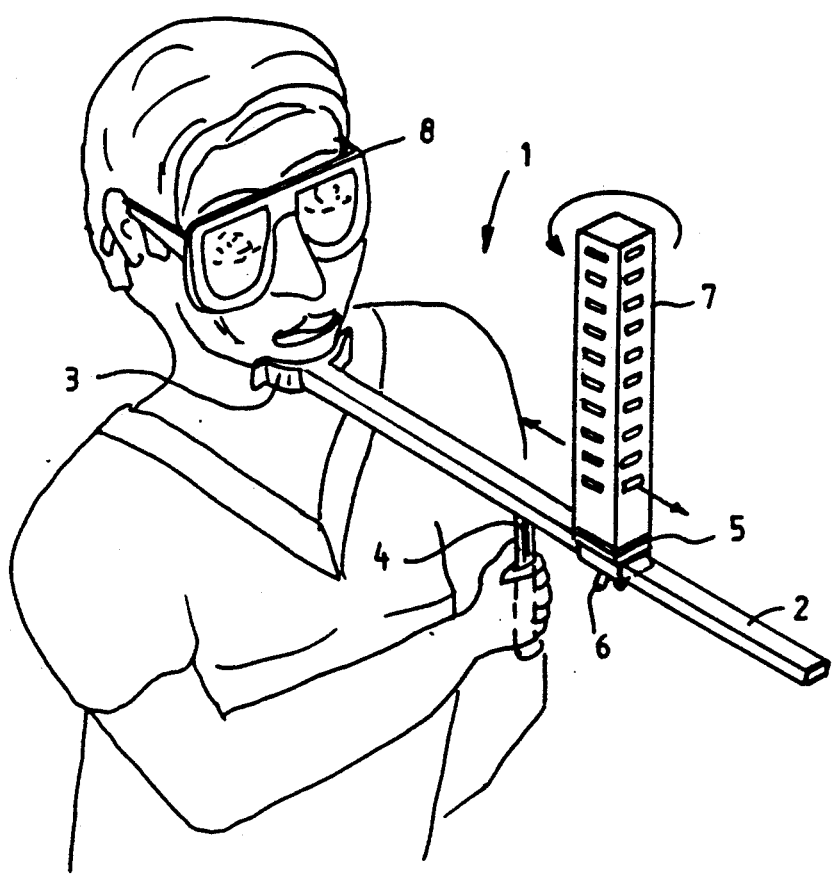
FIG. 1 is a perspective view of an apparatus of the invention in use by a test subject.

Referring now to the accompanying drawings a stereoscopic vision test apparatus 1 is shown to comprise a frame in the form of an elongated rod 2 fitted at its proximal end with a diverging fork formation 3 adapted in use to engage the patient's chin. The rod 2 is further fitted with a grip 4 whereby the patient may hold the apparatus in place to extend substantially horizontally. The apparatus further includes a base formation 5 in sliding engagement with the rod and fitted with a winged stud 6 by means of which the base formation may be clamped against sliding at a preferred disposition from the proximal end of the rod. A stereogram support structure 7 is mounted on the base formation to be rotatable about an axis extending normally to the longitudinal direction of the rod thereby to allow one of the faces of the stereogram support structure to be placed in the line of vision of the patient.

Figure 2A:
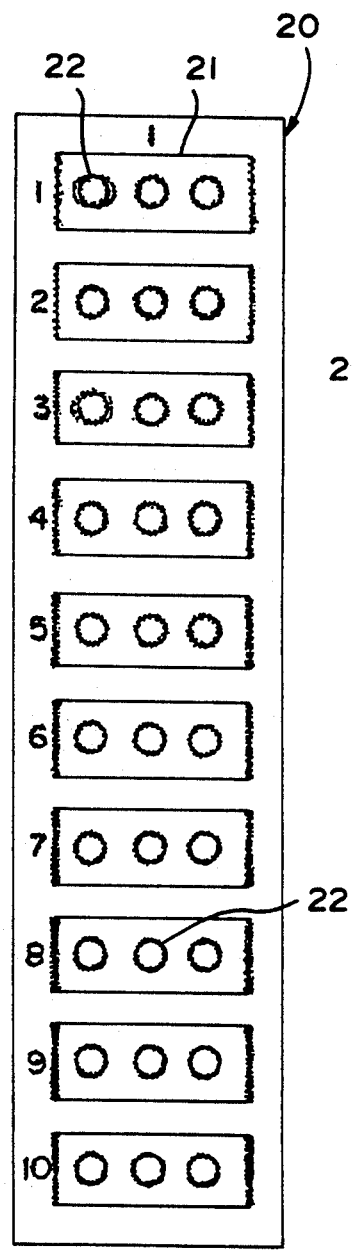
FIGS. 2A–2C are a plan view of three stereograms used in conjunction with the apparatus of FIG. 1 and also forming an integral part of the apparatus of FIG. 2.
Figure 2B:
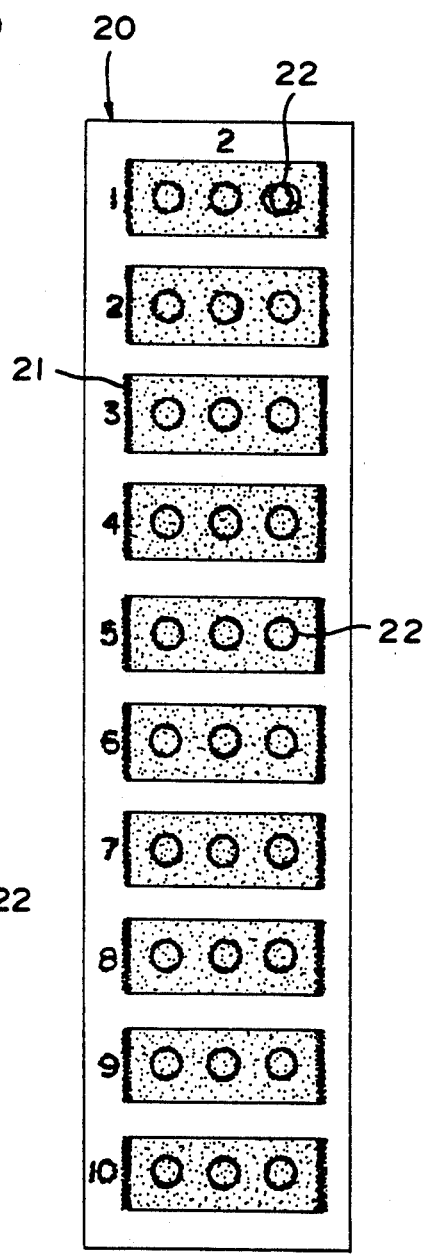
Figure 2C:
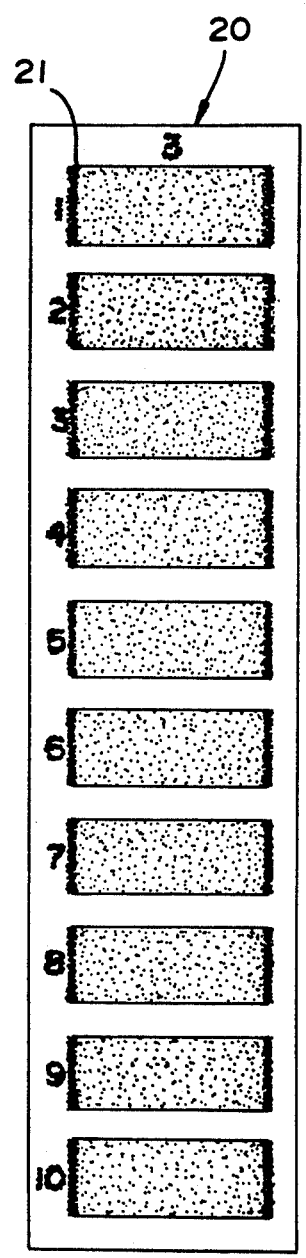

In FIGS. 2A, 2B and 2C three standardised stereogram plates are illustrated.

Each of the plates 20 defines ten rectangular stereograms [some indicated at 21] and each stereogram features one circular form [some of which are indicated by 22] which is presented in stereo disparity form. In the plates marked 1 and 2 each stereogram also features two circular figures which are represented in regular non-disparate form. In the plate marked 3 all of the representation zones feature a random dot pattern but in each stereogram a circular figure is represented in stereo disparity form which circles are all recognisable by a person with a high degree of stereo acuity when viewing the stereograms through dissociating polarised lenses.

In the plate marked 2 in FIGS. 2A, 2B and 2C the circular figures are presented against a noise background constituted by randomly spaced dots while the plate 1 presents a clear background. The principles involved in producing the three types of stereograms which are shown in FIGS. 2A, 2B and 2C are known to the trade and as such do not form part of the invention. The layout of the stereoplates of FIGS. 2A, 2B and 2C has, however, not been suggested before. The standardising of the plates in FIGS. 2A, 2B and 2C so that each contains the same general configuration and graded level of stereo disparity of the stereoforms thereon accordingly forms part of the present invention. The position of the circle with the disparity differs in the various stereograms so as to minimize the risk of correct answers through guessing.

The disparities in each test plate differs in a descending order. The disparities are measured in terms of seconds of arc at 40 cm and were selected in the various stereograms to be as follows:

No. 1 being 400"
No. 2 being 200"
No. 3 being 140"
No. 4 being 100"
No. 5 being 70"
No. 6 being 50"
No. 7 being 40"
No. 8 being 30"
No. 9 being 25"
No. 10 being 20".

In using the apparatus of FIG. 1 the test subject is given a pair of dissociating polarised lenses 8 which are in crossed or uncrossed mode and he is asked to name the position of the circle which stands out either in front or behind the reference ground in each stereogram while the time for completion of the test [i.e. the ten stereograms of a particular plate] is taken. The test may then be repeated with the polarised lenses in the opposite mode. The rings with stereo disparity will be perceived to recede relative to the plane of fixation when using lenses in the uncrossed mode and to stand out in front of the reference ground when using dissociating polarised lenses in the crossed mode.

Figure 3:
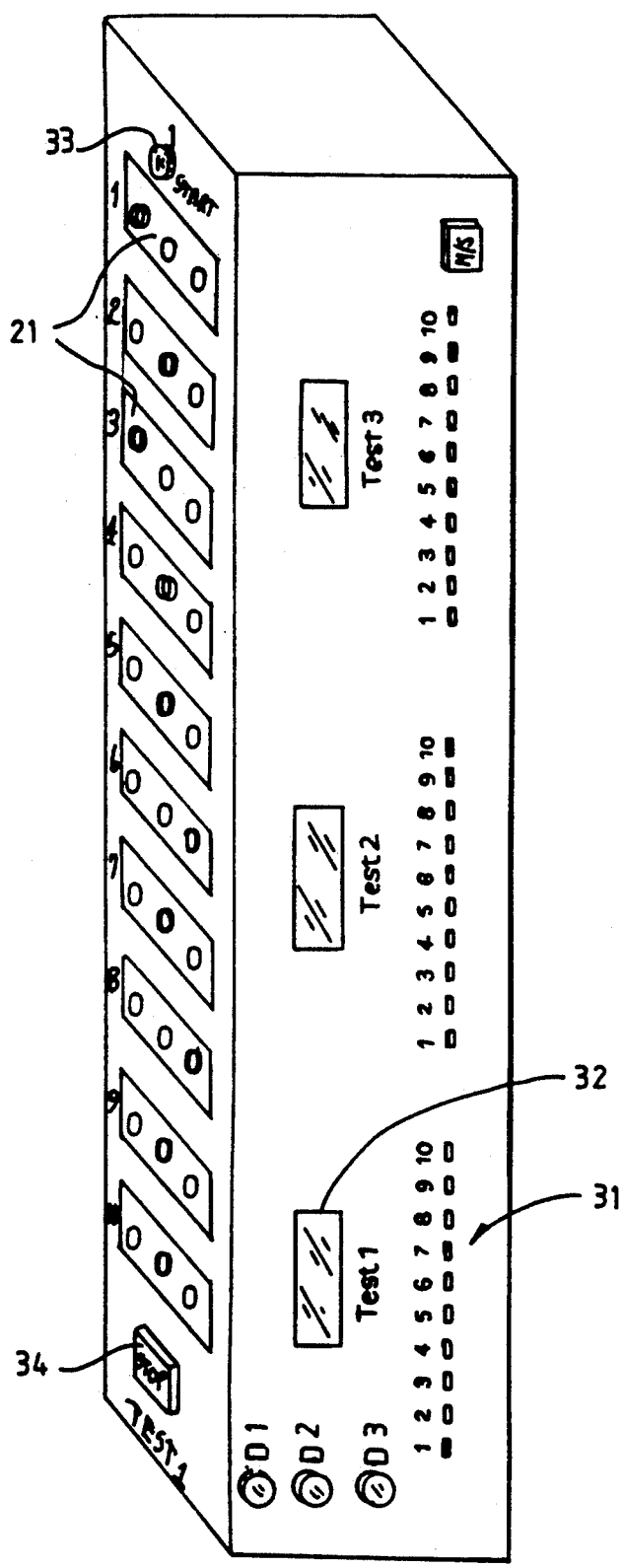
FIG. 3 is a perspective view of an integrated stereogram support structure and display according to the second embodiment of the invention.

Depending on the degree of the patient's stereo acuity he or she will be able to identify correctly the figures having stereo disparity up to a particular degree of stereo disparity. From the time taken to perform the test and the degree of stereo acuity valuable information can be obtained. Four types of responses can be observed, namely the quick-accurate who performs best on the test, the slow-inaccurate who performs worse, and two groups inbetween, the quick-inaccurate and the slow-accurate. This distinction can be used in any remedial therapy where space and time considerations are critical. In FIG. 3 is illustrated an electronic version of the stereogram support of FIG. 1. In this version each of the left, middle and right position of the representation zones 21 of each panel are fitted with membrane switches [not shown] which are operatively connected to light emitting diodes placed in juxtaposition at display windows 31. Each panel 30 also has a timer 32, a timer starter 33 and timer stop 34 associated therewith. A test is conducted by the patient starting the timer by pressing the start switch 33 and then touching the symbol perceived to be displaced when viewed through polarised lenses and stopping the timer by pressing switch 34 after reaching zone 10. A correct answer causes a light emitting diode in the corresponding display window to be energised and a wrong answer results in the display window remaining unlit. The apparatus may preferably be fitted with a memory to allow the supervisor to "score" the test after completion by depressing the switches marked "D". The lights may alternatively remain lit until de-energised. The switches at each position on each stereogram are also associated with a buzzer to give an audible signal to the test subject that his or her answer had been recorded.

This test differs from other tests of stereopsis in that it combines three types of test target, namely

[a] one which consists of form which is recognisable monocularly against a formless background with high contrast;

[b] one which consists of form which is recognisable monocularly against a random dot background and with lower contrast; and

[c] one which consists of random dots where form is not recognisable monocularly and where there is no contrast.

Contrary to existing types of test targets which differ in shape, size and configuration, as well as in respect of their graded acuity, these variables have been made constant in the plates preferably used according to the invention.

Existing test instruments have been manufactured in book-form to be held like a book, which makes it difficult to control for a set working distance. The instrument of the invention provides a rod and chin bar to ensure a standard working distance and ease of operation since the test plates are housed on the long vertical sides of a rectangular hexahedron which is mounted to the rod of the instrument in such a way that it can rotate and engage at 90° intervals.

In existing stereotests use is only made of cross polarized viewers which facilitate the testing of stereoacuity in front of the plane of regard, but not the testing of stereoacuity behind the plane of regard. The invention also addresses this aspect.

The existing stereotests have not incorporated the element of time of completion of the tests and have not recognised the importance of this in relation to the stereoacuity achieved. By interfacing three different stereotests with the same shapes, configurations and graded acuities, but differing with respect to their degrees of monocular form recognition and contrast, it is possible to assess the effects of these differences on stereoacuity and the time it takes to complete such tests.

Clearly many variations of the invention may be devised without thereby departing from the spirit or concept of the invention. Thus, one of the sides of the support may include preliminary tests of near working distance visual acuity of the right eye on its own, the left eye on its own and both eyes together as well as non-stereoscopic tests of binocular vision.

I claim:

1. An apparatus suitable for use in conducting stereoscopic vision tests, the apparatus comprising an elongated frame structure defining a proximal end and a distal end, the proximal end being adapted to engage against the body of a test subject and the frame being adapted towards its distal end to carry a stereogram support structure in axially displaceable relationship relative to the proximal end to allow the stereogram to be placed at a selected distance from the proximal end of the apparatus, the support structure being in the form of a carrousel-like arrangement adapted to carry a plurality of stereograms and allowing a selected stereogram to be brought into a selected line of vision when the apparatus is supported in operative disposition against the face of a test subject.

2. The apparatus of claim 1 wherein the support structure is in the form of an irregular polyhedral structure defining a plurality of oblong rectangular faces, mounted for rotation about its longitudinal axis and disposed to extend normally upwardly from the rod when the apparatus is in operative disposition, the support structure thereby being adapted to be rotated about its longitudinal axis to bring a selected face into the normal line of vision of the test subject.

3. An apparatus suitable for use in conducting stereoscopic vision tests, the apparatus comprising an elongated frame structure defining a proximal end and a distal end, the proximal end being adapted to engage against the body of a test subject and the frame being adapted towards its distal end to carry a stereogram support structure in axially displaceable relationship relative to the proximal end to allow the stereogram to be placed at a selected distance from the proximal end of the apparatus, the stereograms used in conjunction with the apparatus comprise a group of three plates each of which features ten stereograms arranged in line with one another and each stereogram featuring one form having stereo disparity, the degree of stereo disparity of the stereo forms in successive stereograms being progressively smaller from one end of the plate to the other.

4. The apparatus of claim 3 in which the first of the stereogram plates the stereo forms are presented as contoured circles against a noise free background, in the second the circles, which are invisible monocularly, are represented against a noise background constituted by random dots and in the third plate the contoured circles are presented against a random dot noise background, and in which, in the first-mentioned two stereogram plates each stereogram zone features two non-stereo forms along with the stereo form and the relative position of the stereo form and non-stereo forms are located in random arrangement, while in the random dot stereogram plate the stereo circle form is randomly placed on either the left, right or center in relation to its reference ground.

5. The apparatus of claim 3 wherein said integrated stereogram support structure is integrated and wherein each form position of each stereogram has associated therewith a membrane switch which is operatively connected to a power source, a visible signal means and an audible signal generator, the support arrangement further including a timer arrangement, and an activator and deactivator for the timer arrangement.

6. An apparatus suitable for use in conducting stereoscopic vision tests, the apparatus comprising an elongated frame structure defining a proximal end and a distal end, the proximal end being adapted to engage against the body of a test subject and the frames being adapted towards its distal end to carry a stereogram support structure in axially displaceable relationship relative to the proximal and to allow the stereogram to be placed at a selected distance from the proximal end of the apparatus, wherein the stereograms used in conjunction with the apparatus comprised a group of three plates, each of which features stereograms arranged in line with one another and each stereogram featuring one form having stereo disparity, the degree of stereo disparity of the stereo forms in successive stereograms being progressively smaller from one end of the plate to the other and in which the first of the stereogram plates the stereo forms are presented as contoured forms against a noise-free background, in the second the forms, which are invisible monocularly, are represented against a noise background by random dots and in the third plate the contoured forms are presented against a random dot noise background and in which in the first-mentioned two stereogram plates each stereogram zone features at least two non-stereo forms along with the stereo form and the relative position of the stereo form and non-stereo form are located in random arrangement, while in the random dot stereogram plate, the stereo form is randomly placed on either the left, right or center in relation to its reference ground.

7. The apparatus of claim 6 characterised in that the apparatus is portable and comprises a frame in the form of a rod which optionally includes a transversely extending grip formation for use in holding the rod in operative disposition.

8. The apparatus of claim 7 wherein the proximal end of the rod is adapted in use to engage against the face of the test subject by being fitted with a diverging fork formation at the proximal end thereof.

9. The apparatus of claim 7 wherein the stereogram support structure is equipped with a base formation adapted to be mounted in sliding relationship on the rod and a clamp arrangement for use in clamping the base formation at a selected disposition relative to the proximal end of the rod.

10. The use of the apparatus as claimed in any one of claims 1–9 in a method of testing the stereo activity of patient comprising the steps of instructing the patient to start the test by a timer and then touching the figures recognized as having stereoscopic properties when looking at the stereogram through polarized lenses and deactivating the timer when the test is completed.

* * * * *